(12) United States Patent
Wienkers et al.

(10) Patent No.: US 6,979,545 B2
(45) Date of Patent: Dec. 27, 2005

(54) METHOD FOR DETERMINING CHEMICAL REACTIVITY

(75) Inventors: Larry C. Wienkers, Portage, MI (US); Michael J. Hauer, Kalamazoo, MI (US); Dennis E. Epps, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 561 days.

(21) Appl. No.: 09/972,520

(22) Filed: Oct. 5, 2001

(65) Prior Publication Data

US 2002/0110919 A1 Aug. 15, 2002

Related U.S. Application Data

(60) Provisional application No. 60/238,238, filed on Oct. 5, 2000.

(51) Int. Cl.[7] .............................................. G01N 33/53
(52) U.S. Cl. ......................................... 435/7.1; 435/4
(58) Field of Search ........................ 435/7.1, 2, 4, 7.4, 435/7.5, 7.6, 7.8, 7.9, 7.91, 7.92, 7.93, 7.94, 435/7.95; 436/518; 604/500

(56) References Cited

U.S. PATENT DOCUMENTS

| | | | | |
|---|---|---|---|---|
| 5,312,729 A | * | 5/1994 | Allen et al. ................... | 435/7.9 |
| 5,919,786 A | * | 7/1999 | Iwasawa et al. ............. | 514/256 |
| 6,468,657 B1 | * | 10/2002 | Hou et al. ................... | 428/403 |

FOREIGN PATENT DOCUMENTS

WO    WO99/61910    12/1999    .......... G01N 33/53

OTHER PUBLICATIONS

WO99/61910.*

Graham, SL et al., "Topically active carbonic anhydrase inhibitors. 3 Benzofuran-and indole2-sulfonamides." Journal of Medicinal Chemistry, vol. 33, No. 2, pp. 749-754, Feb. 1990.*

Epps, DE et al., "A competitive fluorescence assay to measure the reactivity of compounds," Analytical Biochemistry, vol. 295, No. 1, pp. 101-106, Aug. 2001.*

O'Connor, JE et al., "A Flow Cytometric Assay for Intracellular Nonprotein Thiols Using Mercury Orange," Cytometry 9, 529-53 (1988).*

Cnubben, Nicole H P et al., "Influence of the halogen-substituent pattern of fluoronitrobenzenes on their biotransformation and capacity to induce methemoglobinemia," Toxicology and Applied Pharmacology, vol. 139, No. 1, pp. 71-83, 1996.

(Continued)

*Primary Examiner*—Long V. Le
*Assistant Examiner*—Ann Y. Lam
(74) *Attorney, Agent, or Firm*—Charles W. Ashbrook; Austin W. Zhang (57) ABSTRACT

A method for screening chemical compounds for electrophilic properties comprising the steps of:
(a) providing an assay having one or more reaction vessels;
(b) adding a predetermined amount of separate chemical compounds for screening to each reaction vessel;
(c) adding a predetermined amount of a surrogate chemical marker to each reaction vessel and allowing said separate chemical compounds and surrogate chemical marker to incubate for a period of time;
(d) adding a reactive chemical to each reaction vessel which is capable of reacting with residual surrogate chemical marker such that the amount of residual surrogate chemical marker present after step (c) can be quantitatively or qualitatively measured; and
(e) quantitatively or qualitatively measuring said residual chemical marker is provided.

15 Claims, 3 Drawing Sheets

Intrinsic assay variability for the mercury orange S-glutathionyl derivative from six 96 well microtiter plates (N=576).

OTHER PUBLICATIONS

Epps, DE et al., "A competitive fluorescence assay to measure the reactivity of compounds," Analytical Biochemistry, vol. 295, No. 1, pp. 101-106, Aug. 2001.

Graham, SL et al., "Topically active carbonic anhydrase inhibitors. 3 Benzofuran- and indole-2-sulfonamides." Journal of Medicinal Chemistry, vol. 33, No. 2, pp. 749-754, Feb. 1990.

O'Connor JE, et al., "A Flow Cytometric Assay for Intracellular Nonprotein Thiols Using Mercury Orange," Cytometry 9, 529-532 (1988).

Portoghese, PS, et al., "Reactivity of glutathione with alpha, beta-unsaturated ketone flavouring substances." Food and Chemical Toxicology: An international Journal Published for the British Industrial Biological Research Association, vol. 27, No. 12, pp. 773-776, Dec. 1989.

Vukovic, V et al., "Microregional heterogeneity of nonprotein thiols in cervical carcinomas assessed by combined use of HPLC and fluorescence image analysis." Clinical Cancer Research: An Official Journal of the American Association for Cancer Research, vol. 6, No. 5, pp. 1826-1832, May 2000.

* cited by examiner

Figure 1. Intrinsic assay variability for the mercury orange S-glutathionyl derivative from six 96 well microtiter plates (N=576).

Figure 2. Representative LC/MS/MS chromatograms from the LLQ, (10 µL of screen material injected), 2-Bromo-4-nitrothiazole GSH adduct: (A) full-scan TIC, (B) full-scan extracted ion chromatogram for glutathione adduct, (C) Mass spectra of GSH adduct, (D) MS/MS spectra of GSH adduct.

Figure 2. cont'd

METHOD FOR DETERMINING CHEMICAL REACTIVITY

CROSS-REFERENCE TO RELATED APPLICATION

This application claims the benefit of the following provisional application: U.S. Ser. No. 60/238,238, filed Oct. 5, 2000, under 35 USC 119(e)(i), which is incorporated herein by reference in its entirety.

BACKGROUND OF THE INVENTION

1. Field of the Invention

The present invention is directed to a method for determining the chemical reactivity of a molecule. More specifically, it is directed at a method for determining the electrophilic reactivity of a molecule by a sequence of chemical additions and then quantitatively or qualitatively measuring the electrophilic properties. In particular the invention provides a high throughput toxicity screening method for pharmaceutically active molecules.

2. Technology Description

The current trend in the pharmaceutical industry is to shorten the time scale for all aspects of drug discovery. The impetus for this trend is to respond to the development of combinatorial chemistry techniques combined with a wide variety of in vitro biochemical and cell-based high-throughput screening (HTS) assays. The application of these early discovery methodologies has greatly increased the capacity demands of secondary discovery screening efforts including preclinical studies such as membrane permeability, metabolic stability, and drug-drug interactions.

For many different chemicals, including some drugs, the mechanism of cellular toxicity is via covalent interactions with cellular macromolecules. These reactions are usually dependent upon the facile reaction between an electrophilic carbon of the compound with a nucleophilic moiety of the macromolecule. Potential electrophiles may range in size and chemical structure and react with macromolecules through a variety of mechanisms. If the determination of cellular toxicity can be made as early as possible during the drug discovery process, this can have the effect of quickly reducing developmental costs on molecules which are potentially toxic.

Reduced glutathione ($\gamma$-glutamylcysteineglycine, GSH) is well known to interact with reactive compounds and thus plays a critical role in detoxification of electrophilic compounds in vivo. The reaction between GSH and electrophilic compounds may occur via non-enzymatic as well as enzymatic (glutathione S-transferase) processes. However for the uncatalyzed reaction between GSH and a series of electrophiles, the rates of reaction depend solely upon the chemical nature of each electrophile. In this light, the non-enzymatic conjugation between glutathione and an electrophile may be used as a surrogate marker to assess the potential reactivity of novel chemical entities (NCEs) with cellular macromolecules in vivo.

WO99/61910 discloses a high throughput, on-line, pulsed ultrafiltration-mass spectrometric method for determining whether a compound has predetermined characteristics that would make it suitable for a specific purpose, e.g., drug development. The method is used for rapid screening of drugs or other compounds to determine the extent of their metabolism and to characterize their primary metabolites. If reactive and potentially toxic metabolites are formed the metabolites can be reacted with glutathione and then detected on-line using mass spectrometry in a rapid assay to assess the potential for toxicity.

In the field of flow cytometry, determination of the presence of GSH by reaction with mercury orange has been suggested. See, for example, "A Flow Cytometric Assay for Intracellular Nonprotein Thiols Using Mercury Orange", Cytometry 9, 529-532 (1988).

Despite the above teachings, there still exists a need in the art for a high-throughput compound independent assay and method to identify potential electrophilic compounds as early as possible in drug discovery.

BRIEF SUMMARY OF THE INVENTION

In accordance with the present invention a novel method for the high-throughput screening of compounds for electrophilicity is provided. More specifically, the method comprises the steps of (a) providing an assay having one or more reaction vessels;
(b) adding a predetermined amount of separate chemical compounds for screening to each reaction vessel;
(c) adding a predetermined amount of a surrogate chemical marker to each reaction vessel, preferably such that the molar ratio of separate chemical compound to surrogate chemical marker is greater than 1 to 1, and allowing said separate chemical compounds and surrogate chemical marker to incubate for a period of time;
(d) adding a chemical to each reaction vessel which is capable of reacting with residual surrogate chemical marker such that the amount of residual surrogate chemical marker present after step (c) can be quantitatively or qualitatively measured; and
(e) quantitatively or qualitatively measuring said residual surrogate chemical marker.

In particularly preferred embodiments, the surrogate chemical marker is $\gamma$-glutamylcysteineglycine and the chemical added in step (d) is mercury orange [1(4-chloromercuryphenyl-azo-2-naphthol)]. In still additionally preferred embodiments, step (e) comprises exposing the reaction vessels to electromagnetic waves in either the visible or ultraviolet wavelength regions and noting if the reaction vessels have undergone a color change.

In another embodiment of the present invention, an assay system or kit is provided. The system or kit comprises the following components:

(a) one or more reaction vessels;
(b) a surrogate chemical marker; and
(c) a reagent which is capable of reacting with residual surrogate chemical marker, each in an amount sufficient to conduct at least one assay.

In preferred embodiments, the kit contains 1, 6, 12, 24, 48, 96, 256, 512 or 1028 reaction vessels.

In still another embodiment of the present invention, a method for reducing the electrophilic properties of a molecule is provided. The method includes the steps of:

(a) providing a chemical compound;
(b) combining a surrogate chemical marker with said chemical compound, preferably such that the molar ratio of said chemical compound to said surrogate chemical marker is greater than 1 to 1, and allowing said chemical compound and surrogate chemical marker to incubate for a period of time;
(c) adding a chemical to the reaction vessel used in step (b) which is capable of reacting with residual surrogate chemical marker such that the amount of residual surrogate chemical marker present after step (b) can be quantitatively or qualitatively measured;

(d) determining if the chemical compound has electrophilic properties;
(e) determining the site of electrophilicity on the compound; and
(f) modifying the molecule so that it is no longer has electrophilic properties.

Once the molecule is modified, because of reduced toxicity it then may be useful for medical treatment.

An object of the present invention is to provide a method for determining the electrophilicity of a chemical compound.

Still another object of the present invention is to provide a diagnostic or test kit for determining the electrophilicity of chemical compounds.

A further object of the present invention is to provide a method for reducing the potential toxicity of a chemical compound.

These, and other objects, will readily be apparent to those skilled in the art as reference is made to the drawings and detailed description of the preferred embodiment.

BRIEF DESCRIPTION OF THE DRAWINGS

FIG. 2A: full-scan TIC: FIG. 2B: full-scan extracted ion chromatogram for glutathione adduct: FIG. 2C: Mass spectra of GSH adduct: and FIG. 2D: MS/MS spectra of GSH adduct.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The current invention relates to a method for determining the relative chemical reactivity (i.e., electrophilicity) of novel chemical entities in early drug discovery using an assay with conventional microtiter plates and microtiter fluorescent plate-reading equipment with standard interference filter. The assay relies upon the quantitation of residual surrogate chemical marker after co-incubation with a potentially reactive (i.e., electrophilic) discovery compound. In a preferred embodiment, the assay is a modification of a known flow cytometry procedure, the formation of a mercury orange S-glutathionyl derivative at room temperature.

The first step of the process is to provide an assay having one or more reaction vessels. In practice commercially available assay plates can be used. Such plates typically have either 1, 6, 12, 24, 48, 96, 256, 512 or 1028 reaction vessels. Once the assay is assembled, the chemical compounds for which electrophilicity is to be evaluated are added to each vessel. In practice each vessel contains one compound but variations are possible (i.e., a single chemical compound can be added to multiple vessels for the purpose of confirming results).

Thereafter the surrogate chemical marker is added to each reaction vessel. In practice the marker is either a protein, enzyme, DNA, any component or fragment thereof or mixture thereof. In particularly preferred embodiments, the marker is gamma-glutamylcysteineglycine (GSH). The reactivity of GSH with electrophilic compounds is discussed above. The amount of GSH added to each reaction vessel should be less than the amount of the test compound because, if the GSH fully reacts with the compound then it should be fully consumed by the reactivity. The molar ratio used to facilitate these reactions is recognized not to reflect physiological conditions, in which GSH concentrations (10 mM) normally exceed that of the potential electrophile. However, the underlying premise of the inventive method (i.e., the innate chemically electrophilicty of a chemical) is valid using reduced GSH as a surrogate nucleoplile, moreover under these experimental conditions electrophilic compounds are readily and accurately identified as being reactive via measurement of remaining GSH. In addition to GSH, n-acetyl cysteine or cysteine could be selected. Further, any chemical or biological compound containing a free sulfhydryl or similarly chemically reactive group, for example beta-mercaptoethanol, could also be used.

Depending on the selection of the compound for screening and the chemical which is also added to compete with the compound for screening for GSH reactivity, the GSH is typically added to the reaction vessel in a solvent. For example, when the inventive method utilizes GSH and mercury orange, the solvent selected is acetonitrile. In other embodiments the surrogate chemical marker may be added in neat form, dimenthyl sulfoxide buffered solutions, and the like.

It is further understood that the order of addition of chemical compound and surrogate chemical marker is not critical, i.e., the marker can first be added to the vessel followed by addition of the chemical compound and vice versa. While not required, to improve the efficiency and speed of results, it is preferred that the relative amounts of surrogate chemical marker and chemical compound are such that a molar excess of chemical compound is present.

Once the compound and the marker have both been added to the same vessel, they are allowed to incubate under conditions mimicking the human (or animal) physiological system. In practice, the incubation temperature is room temperature and the time period for incubation can be between 1 and 1000 minutes, with a time period of 30 to 240 minutes being more preferred and 60 minutes being most preferred.

Either before, at the time the residual surrogate chemical marker is added, or after the incubation period, a chemical which is capable of reacting with residual surrogate chemical marker such that the amount of residual surrogate chemical marker present after incubation can be quantitatively or qualitatively measured is added. In one preferred embodiment, when GSH is used as the marker, mercury orange [1(4-chloromercuryphenyl-azo-2-naphthol)] (HgO) is used as the chemical as the reaction between mercury orange and GSH forms a mercury orange S-glutathionyl derivative which emits red fluorescence upon excitation with visible, or ultraviolet light. The major drawback for using the HgO/GSH reaction is that the resulting S-glutathionyl derivative is highly insoluble and thereby difficult to potentially analyze. However, when administrating the HgO it is preferably first formed in a solution of acetone and just before using the HgO/acetone solution is diluted in acetonitrile. A particularly effective ratio of acetone to acetonitrile is approximately 2:5. This ratio enables the resulting derivative to remain in solution long sufficiently long for analysis (i.e., greater than 15 minutes.)

Other chemicals which can be selected include fluorescent maleimides (fluorescein-5-maleimide or coumarin maleimide) and other fluorescent materials (i.e., any molecule which can react with the residual marker to generate some type of entity which can then be qualitatively or quantitatively analyzed).

Determining when the different chemicals are to be added is largely a result of the specific chemicals which are selected for use in the screening procedure. For example, when GSH and HgO are selected, it is preferred that the HgO is added after the GSH and compounds for screening have had time to incubate. When fluorescent maleimides and GSH are selected, both of these entities can be added to the compounds for screening at about the same time. In fact, for this embodiment, the fluorescent maleimides may even be added to the reaction vessel prior to the addition of the compound to be screened and prior to the GSH addition.

After the addition of the reactive chemical to the reaction vessel, the vessel is quantitatively or qualitatively analyzed to determine if the original chemical compound sufficiently reacted with the marker. For example, the vessels are excited with wavelengths from either the ultraviolet or visible light spectrum, and more preferably ultraviolet light. As discussed above, the reaction of GSH with HgO results in the emission of red fluorescence when excited with ultraviolet light. The emission of such fluorescence is an indication that the GSH has not sufficiently reacted with the original chemical compound, which is evidence that the original compound is not electrophilic (i.e., less likely to be toxic). By comparison, if the resulting reaction vessel does not show any type of reaction between the GSH and HgO, or if the reaction is greatly reduced, this indicates that the original compound does, in fact, react with the GSH and hence is electrophilic (i.e., more likely to be toxic). Analogous results would be expected using other markers and reactive chemicals (i.e., not the chemical compound for which electrophilicity is being determined) as the GSH/HgO formed complex is considered merely representative of the inventive concept.

The above method is capable of high throughput screening for electrophilicity. This is a great benefit for drug development as possible candidates can be removed from development earlier in the process, thereby saving the drug developer valuable time and money resources.

In addition to the qualitative analysis (i.e., color change) discussed above, the inventive method can be used to quantitatively determine the degree of electrophilicity. For example, a quantitative measure of the intensity of fluorescence to determine the degree of electrophilicity can also be determined using known analytical equipment and techniques such as fluorescence micro plate readers. In addition, a mass spectroscopy method can be used to determine the degree of electrophilicity (for example, by comparison against a benchmark for residual marker) and the location on the molecule which is electrophilic. In the area of electrophilicity degree, when GSH is selected as the marker, a benchmark value of less than 20% residual GSH after reaction with the initial chemical test compound may be selected.

In using a quantitative method such as mass spectroscopy, the invention provides the additional benefit of allowing for modification of a molecule to reduce its toxicity. For this aspect of the invention, once it is determined that the molecule is electrophilic, the quantitative technique is used to determine the site of electrophilicity on the molecule. Determination of this is considered to be well within the skill of the artisan. To render the molecule less toxic, the site of electrophilicity can be modified to render it non-electrophilic. For example, this can be accomplished by replacing a substituent on the molecule at the site of electrophilicity (and which is believed to be responsible for the electrophilicity) with one that would render it less or non-electrophilic. In the field of drug discovery this can be a benefit as a compound that would have been eliminated because of toxicity problems can then be modified to where it will once again be a potential candidate. Once the toxicity of the compound has been reduced, assuming that it has an appropriate safety and efficacy profile it can be used for administration to a patient to treat a disease.

The invention is described in greater detail by the following non-limiting examples.

EXAMPLE 1

An electrophilic compound is a compound that has the ability to covalently bind to a nucleophile by accepting both bonding electrons from that reaction partner. The relative reactivity of an electrophilic compound is conceptually related to Lewis acidity. However, whereas Lewis acidity is governed by relative equilibrium constants, electrophilicity is a relative measure of reactivity of different compounds towards a common substrate (usually involving attack at a carbon atom). To insure that the reduced glutathione (GSH) screen unequivocally differentiates reactive chemicals from non-reactive compounds, 76 structurally diverse compounds are tested using a GSH screen. The library is comprised of 52 compounds initially deemed non-reactive, 19 chemicals previously demonstrated to react with cellular macromolecules including glutathione upon metabolic activation and 5 compounds described as electrophiles.

The test compounds as listed in Table 2 to be screened are dissolved in dimethyl sulfoxide (DMSO) to a final concentration of 10 mM, and 2 $\mu$L is transferred to the wells of a polypropylene 96-well microtiter plate. GSH stock solution (1.525 mM) is prepared daily in 10 mM ammonium acetate buffer (pH 7.4). GSH working solution (208 $\mu$M) is prepared by diluting the stock solution with acetonitrile just prior to use. Mercury orange (HgO) stock solution (470 $\mu$M) is prepared in acetone and stored at 4° C. HgO working solution (66.6 $\mu$M) is prepared by diluting the stock solution in acetonitrile just prior to use. A 48 $\mu$L aliquot of the GSH working solution is pipetted into the 96-well tray containing the test compounds to yield a final concentration of 200 $\mu$M GSH. The reaction of the test compound with the GSH is allowed to proceed for 1 h at room temperature after which time an aliquot of HgO is added to each reaction well to yield a final concentration of 50 $\mu$M GSH/HgO. The GSH/HgO reaction is allowed to stand for 5 min at room temperature and analyzed using fluorescence micro plate reader detection (28° C., 485ex, 612em). Assay linearity is investigated by preparing a GSH standard curve in the concentration range 0 to 50 $\mu$M (final concentration). Routine sample analysis is achieved using a Biomek 2000 biorobotic system configured with six 96-well plates and 2 reagent reservoirs.

Analytical separation is accomplished using a HPLC system equipped with a Perkin Elmer (Norwalk, Conn. USA) series 200 autosampler (96-well) and Perkin Elmer series 200 quantanary HPLC pump fitted with a Waters (Milford, Mass. USA) Symmetry C8 column (2.1×150 mm). The mobile phase consists of solvent A (900:98:2 water:methanol:acetic acid, v:v:v) and solvent B (900:98:2 methanol:water:acetic acid). The gradient employed is as follows: 100% A for 1.2 min, linear to 0% A in 0.1 min, and hold for 8 min. A constant flow rate of 0.5 mL/min is maintained throughout the analysis. The column effluent to the MS is diverted to waste for 0.5 min post injection. Mass spectral characterization of the electrophilic "softspot" is accomplished using a Finnigan LCQ ion-trap (San Jose, Calif. USA). The standard Finnigan electrospray interface is operated in the positive ion mode with nitrogen (99.9% pure, AGA, Maumee, Ohio USA) employed as a drying gas at a sheath pressure of 80 psi and auxiliary flow rate of 20 mL/min. The heated capillary is set at 250° C. and 4.5 kV is applied to the electrospray needle. A two-event scan is used. The first event is a full-scan MS (m/z 200 to 800). The second event is a tandem MS dependent scan. The dependent scan mode uses criteria from the previous scan to select the target peak for MS/MS. Those peaks that exceeded the minimal signal of 1×106 counts are selected for MS/MS using a 2 amu isolation width and 18% relative collision energy.

Figure 1:
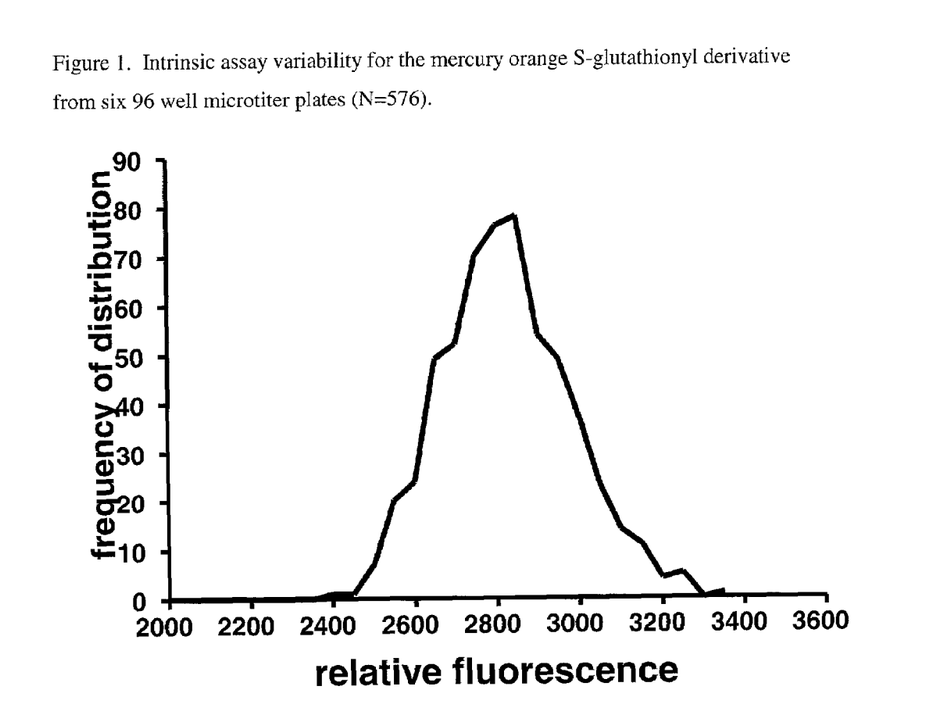
FIG. 1 is a graph of the intrinsic assay variability for the mercury orange S-glutathionyl derivative from six 96 well microtiter plates as described in Example 1.

Distribution of fluorescence intensity and statistical analysis of the reproducibility of the GSH adduct formation is carried out using six 96 well microtiter plates reveals very little inter-plate variability. The results of this analysis reveals that fluorescence intensity for the 576 data points are gaussian in nature, with a mean fluorescence intensity of 2824 fluorescence units, and a CV of 5.53% (FIG. 1). There is no significant difference between the six plates and the intraplate variability is minimal with the coefficient of variability for each plate being 7 percent or less (Table 1).

TABLE 1

Inter- and Intraplate Variability.

| Plate Statistics | Plate 1 | Plate 2 | Plate 3 | Plate 4 | Plate 5 | Plate 6 | Combined |
|---|---|---|---|---|---|---|---|
| Mean (AFU*) | 2774 | 2776 | 2781 | 2775 | 2880 | 2960 | 2824 |
| Standard Deviation | 164.7 | 194.3 | 109.9 | 110.6 | 127.4 | 105.3 | 156.1 |
| Coefficient of Variation | 5.94% | 7.00% | 3.95% | 3.99% | 4.42% | 3.56% | 5.53% |

Compounds are then identified as elelctrophiles based upon a predetermined criteria of GSH consumption (e.g., <20% GSH remaining).

TABLE 2

List of compounds (N = 76) to be evaluated for potential reactivity using the GSH reactivity screen.

| Test Molecule | |
|---|---|
| 1,4-Dichlorobenze | NR |
| 1-Chloro-4-nitrobenzene | NR |
| Cloazapine | NR |
| 4-Chloroanailine | NR |
| 4-Chloroanasole | NR |
| Chlorobenzene | NR |
| 4-Chlorobenzoic acid | NR |
| 4-Chlorobenzonitrile | NR |
| 4-Chlorotoluene, | NR |
| 4-Chlorophenylmaleimide | R |
| Ajmaline | NR |
| Aminobenzotriazole | NR |
| Androsterone | NR |
| Ascorbic acid | NR |
| 3'-Azido-3'-deoxythymidine | NR |
| Benzene | NR |
| Butylated hydroxyanisole | NR |
| Butylated hydroxytoluene | NR |
| Bromocyrptine | NR |
| Caffeine | NR |
| Chloroform | NR |
| Chlorodiazapam | NR |
| Chloropropamide | NR |
| Chlorotheophylline | NR |
| Chlorzoxazone | NR |
| trans Crotonaldehyde | R |
| Cimetidine | NR |
| Ciprofloxacin | NR |
| Clotrimazole | NR |
| Coumarin | NR |
| Debrisoquine | NR |
| Delaveridine | NR |
| Dexamethazone | NR |
| Dextromethorphan | NR |
| Diazapam | NR |
| Diclofenac | NR |
| Erythromycin | NR |
| Estriol | NR |
| 7-Ethoxycouramin | NR |
| Etiocholan-17β-ol-3-one | NR |
| Fluconazole | NR |
| Fluoxetine | NR |
| Furafylline | NR |
| Haloperidol | NR |
| Hydroxyanisole | NR |
| Ketoconazole | NR |
| Phenylmaleimide | R |
| Maleimide | R |
| (S)-Mephenytoin | NR |
| Miconazole | NR |
| α-Naphythalflavone | NR |
| Nifedipine | NR |
| 2-Bromo-4-nitrothiazole | R |
| Olazapine | NR |
| Orphenadrine | NR |
| Papaverine | NR |
| Pergolide | NR |
| Phenytoin | NR |
| p-Nitrophenol | NR |
| Pramipexole | NR |
| Pregenolone | NR |
| Propanolol | NR |
| Progesterone | NR |
| Quinidine | NR |
| Reboxetine | NR |
| Reserpine | NR |
| Styrene oxide | NR |
| Sulfaphenazole | NR |
| Tamoxifen | NR |
| Troleandomycin | NR |
| Taxol | NR |
| Testosterone | NR |
| Theophyline | NR |
| Tolbutamide | NR |
| Toluene | NR |
| Triazolam | NR |

The results of the screen are listed in Table 2, and as anticipated, the compounds that are initially categorized as non-reactive yield negative (i.e., non-reactive (NR)) results. In addition, results from Table 2 demonstrate that the compounds known to require metabolic activation prior to adduction to cellular macromolecules in vivo: acetaminophen (Nelson 1991), benzene (Gut 1996); butylated hydroxyanisole and butylated hydroxytoluene (Thompson 1989); haloperidol (Usuki 1996); 4-chlorobenzonitrile (Ding 1996), chloroform (Guastadisegni 1998); clozapine (Maggs 1996); dicholfenac (Shen 1997), toluene (Ross 1997), phenytoin (Muns 1997), and tamoxifen (White 1995) predictably test as non-reactive compounds in the GSH screen. The lack of discernable reactivity for the 12 compounds that have previously been demonstrated to react with cellular macromolecules is an important limitation associated with the GSH screen. Each of the aforementioned compounds requires a metabolic event to form the penultimate reactive species. The principal enzyme systems implicated in these types of reactions are the cytochromes P450. The cytochrome P450 (CYP) enzymes membrane bound heme containing enzyme which via two electron reduction incorporates one molecule of molecular oxygen into molecules are the principle enzyme system responsible for the generation of reactive species capable of binding with cellular macromolecules. An example of P450 reaction leading to the generation of a highly reactive metabolite is observed with the CYP1A2 mediated formation of aflatoxin B1, 7, 8 epoxide (Heinonen 1996). The current screen is sensitive to innate chemical reactivity of the discovery molecule and does not possess the ability to generate a reactive intermediate. Moreover, a second series of compounds which have been shown to form covalent adducts with GSH; 4-chloro-3-nitrobenzonitrile, 4-chloro-3-nitrophenol, 1-chloro-2,4-dinitrobenzene, 4-chloro-3-nitroanisole, 4-chlorol-3-nitrotoluene, 4-chloro-3-nitroaniline, and 1-chloro-4-nitrobenzene, also test as non-reactive compounds in the screen (table 2). These compounds differ from the first series of 19 compounds in that instead of metabolic activation representing the requisite step prior to reacting with GSH, these compounds are bound to glutathione via a glutathione transferase mediated pathway (Van der Aar 1996).

Figure 2:
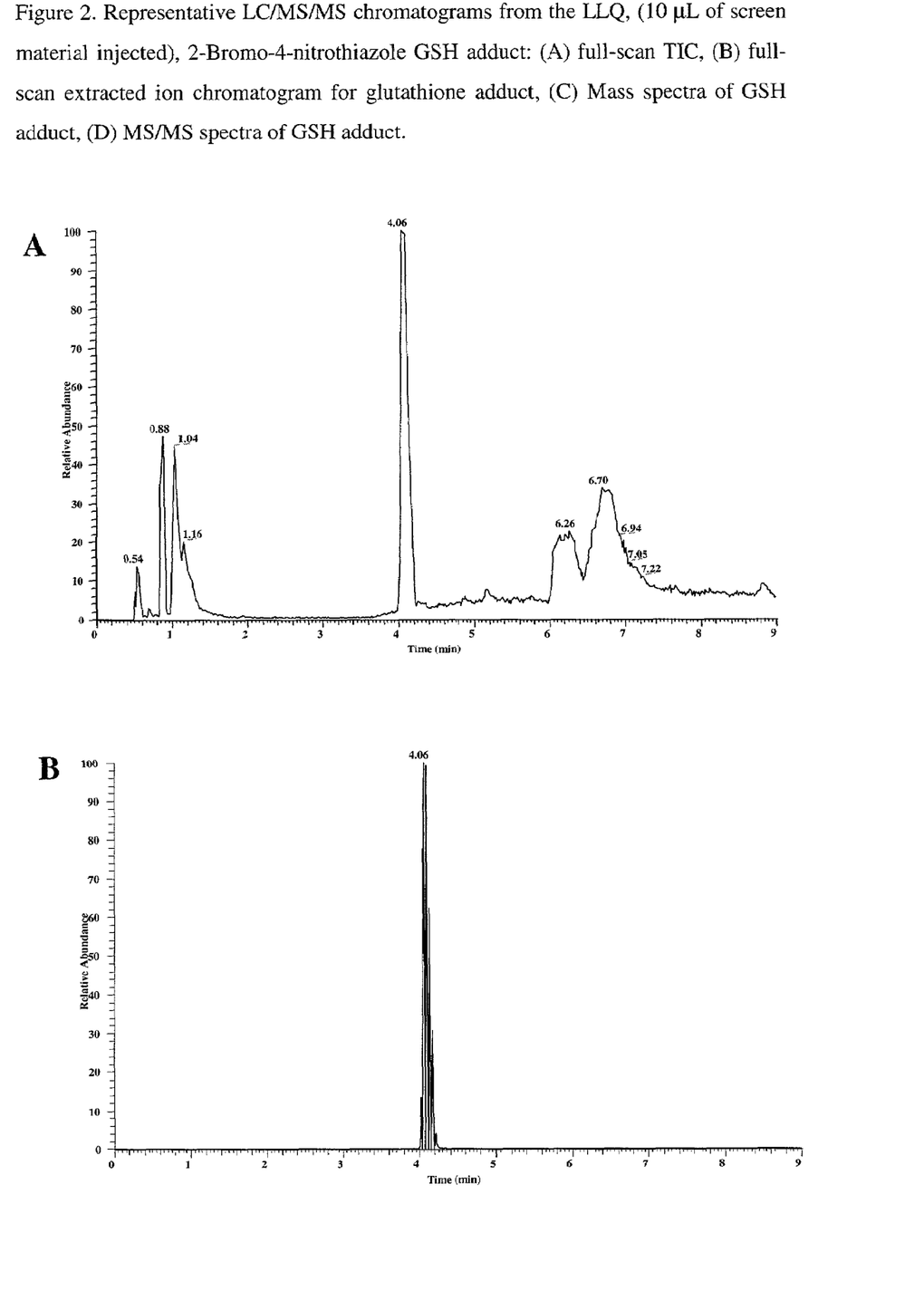
FIG. 2 presents representative LC/MS/MS chromatograms from the 2-Bromo-4-nitrothiazole GSH adduct described in Example 1.

Therefore, of the 76 compounds screened only 5 test as positive (ie., reactive (R)) (Table 2). The reactive compounds include: phenylmaleimide, 4-chlorophenylmaleimide, 2-bromo-4-nitrothiazole, and trans crotonaldehyde. Of these reactive compounds four: maleimide, phenylmaleimide, 4-chlorophenylmaleimide, and trans crotonaldehyde, contain highly electrophilic alpha, beta-unsaturated carbonyl groups which have been demonstrated to react rapidly with glutathione and other nucleophiles via Michael addition (van Iersel 1997). The fifth reactive compound, 2-bromo-4-nitrothiazole, is a bromosubstitued nitro-aromatic ring. However, unlike the chlorosubsituted nitro-aromatic analogs tested, this compound reacts readily with GSH, which suggests a Meisenheimer-like reaction. Characterization of GSH adduction to 2-bromo-4-nitrothiazole is accomplished via injection of the reaction mixture into an LC-MS-ion trap. For this compound and many other compounds to be tested using this method, the primary route of glutathione adduct fragmentation occurs by the elimination of the elements of glycine (−75 amu) and glutamic acid (−129 amu), m/z 361 and 307 respectively, from the MH+ species (FIG. 2). From the mass spectra shown in FIG. 2 it is readily apparent that the addition of GSH proceeds by nucleophilic bromine substitution at the C-2 position.

The results demonstrate the utility of analyzing GSH reactivity screen "hits" and HPLC mass spectrometry as a technique for the rapid determination of electrophilic softspots in a 96-well plate format. The LCQ ion-trap mass spectrometer is capable of doing both a full-scan event, (over a range of approximately 600 Da), and an MS$^2$ SRM scan event within a single duty cycle of 2 s per scan. This capability allows for screening for the presence of GSH/NCE adducts while simultaneously obtaining MS$^2$ of the adduct during a single HPLC run.

EXAMPLE 2

A small aliquot of fluroescein-5-maleimide (FM) in dimethyl sulfoxide (DMSO) is added to a fluorometric cuvette containing 2 ml of phosphate buffered saline at a pH of 7.40. A test compound for screening in DMSO is added to the cuvette, as is a small aliquot of GSH solution. The mixture is exposed to light at 490 nm and emission is observed through a 530 nm bandpass filter. The color of the resulting mixture is observed and the amount of fluorescence is measured. The color is visually compared to a standard which does not include the compound for screening and the fluorescence measurement is compared to this same standard.

A first test compound is of formula:

Visual observation of the cuvette indicates that the level of fluorescence does not appreciably change, and that the reactivity of this compound toward GSH as compared to the FM standard is 2.95 times less. As such, this compound would be considered as not having electrophilic properties.

The same experiment is conducted except the following test compound is evaluated:

Visual observation of the cuvette indicates that the level of fluorescence is appreciably reduced, and that the reactivity of this compound toward GSH as compared to the FM standard is slightly greater. As such, this compound would be considered as having electrophilic properties.

EXAMPLE 3

The experiments of Example 2 are repeated except that coumarin maleimide is selected to replace fluorescein-5-maleimide and the light of excitation is at 370 nm and measured through a 470 nm cutoff filter. The differences in fluorescence are similar to those obtained when using fluorescein-5-maleimide.

Having described the invention in detail and by reference to the preferred embodiments thereof, it will be apparent that modifications and variations are possible without departing from the scope of the appended claims.

What is claimed is:

1. A method for screening chemical compounds for electrophilic properties comprising the steps of:
   (a) providing an assay device having one or more reaction vessels;
   (b) adding a predetermined amount of separate chemical compounds for screening to each reaction vessel;
   (c) adding a predetermined amount of a surrogate chemical marker to each reaction vessel and allowing said separate chemical compounds and surrogate chemical marker to incubate for a period of time;
   (d) adding a reactive chemical to each reaction vessel which is capable of reacting with the surrogate chemical marker such that the amount of the surrogate chemical marker that has not reacted with the separate chemical compounds after step (c) can be quantitatively or qualitatively measured; and
   (e) quantitatively or qualitatively measuring the amount of the surrogate chemical marker that has not reacted with the separate chemical compounds after step (c), wherein the amount of the surrogate chemical marker measured in step (e) that is less than the amount of surrogate chemical marker added in step (c) indicates that the chemical compound is electrophilic wherein said surrogate chemical marker comprises gamma-glutamylcysteineglycine (GSH), n-acetyl cysteine, cysteine, beta-mercaptoethanol or any compound containing a free sulfydryl group, and wherein said reactive chemical in step (d) comprises mercury orange, fluorescein-5-maleimide, coumarin maleimide, fluorophores or compounds capable of reacting with sulthydryl groups.

2. The method according to claim 1 wherein the addition of surrogate chemical marker in step (c) is such that the molar ratio of separate chemical compound to surrogate chemical marker is greater than 1 to 1.

3. The method according to claim 1 wherein said surrogate chemical marker comprises gamma-glutamylcysteineglycine (GSH).

4. The method according to claim 1 wherein said reactive chemical in step (d) comprises mercury orange.

5. The method according to claim 1 wherein step (e) comprises quantitative measuring and wherein said quantitative measuring comprises measuring the surrogate chemical marker that has not reacted with the separate chemical compounds after step (c) by fluorescence spectrophotometry.

6. The method according to claim 1 wherein said surrogate chemical marker comprises GSH, said reactive chemical in step (d) comprises mercury orange and wherein said mercury orange and the GSH that has not reacted with the separate chemical compounds after step (c) react to form an S-glutathionyl derivative which, when excited with light from either the ultraviolet or visible light wavelengths, emits red fluorescence.

7. The method according to claim 6 wherein said GSH and said mercury orange are each distributed in a solvent prior to addition.

8. The method according to claim 7 wherein said solvent for GSH comprises acetonitrile.

9. The method according to claim 7 wherein said solvent for mercury orange comprises a mixture of acetonitrile and acetone.

10. The method according to claim 1 wherein said surrogate chemical marker comprises a protein, enzyme, DNA, any component or fragment thereof or mixture thereof.

11. The method according to claim 10 wherein said reactive chemical in step (d) is capable of reacting with any of the surrogate chemical marker that has not reacted with the separate chemical compounds such that a color change is observed when the reaction takes place in the presence of ultraviolet or visible light wavelengths.

12. The method according to claim 1 wherein steps (b) and (c) are performed before step (d).

13. The method according to claim 1 wherein step (d) is performed before step (c).

14. The method according to claim 1 wherein steps (b), (c), and (d) are performed simultaneously.

15. A method according to claim 1, wherein the surrogate chemical marker is gamma-glutamylcysteineglycine, and wherein the reactive chemical is mercury orange.

* * * * *